(12) United States Patent
Stopek

(10) Patent No.: US 9,364,258 B2
(45) Date of Patent: *Jun. 14, 2016

(54) SINGLE INCISION SURGICAL PORTAL APPARATUS INCLUDING INNER MEMBER

(71) Applicant: Covidien LP, Mansfield, MA (US)

(72) Inventor: Joshua B. Stopek, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,124

(22) Filed: Jan. 28, 2015

(65) Prior Publication Data

US 2015/0150596 A1 Jun. 4, 2015

Related U.S. Application Data

(63) Continuation of application No. 12/796,330, filed on Jun. 8, 2010, now Pat. No. 8,968,190.

(60) Provisional application No. 61/236,652, filed on Aug. 25, 2009.

(51) Int. Cl.
A61B 1/32 (2006.01)
A61B 17/34 (2006.01)
A61B 17/02 (2006.01)

(52) U.S. Cl.
CPC .............. *A61B 17/3423* (2013.01); *A61B 1/32* (2013.01); *A61B 17/02* (2013.01);
(Continued)

(58) Field of Classification Search
CPC ...... A61B 1/32; A61B 17/02; A61B 17/0218; A61B 2017/0225; A61B 17/3423; A61B 2017/3429; A61B 17/3431; A61B 2017/3445; A61B 2014/3486
See application file for complete search history.

(56) References Cited

U.S. PATENT DOCUMENTS 4,112,932 A 9/1978 Chiulli
4,402,683 A 9/1983 Kopman
(Continued)

FOREIGN PATENT DOCUMENTS

EP 0950376 A1 10/1999
EP 1774918 A1 4/2007
(Continued)

OTHER PUBLICATIONS

European Search Report EP08253236 dated Feb. 10, 2009.
(Continued)

*Primary Examiner* — Larry E Waggle, Jr.

(57) ABSTRACT

A surgical apparatus includes a housing member and an inner member. The housing member includes an expandable material that is adapted to transition between a compressed condition and an expanded condition. In the expanded condition, an outer surface of the housing member is adapted for a substantial sealing relationship with tissue upon insertion of the housing member within the tissue for accessing an underlying tissue site. The housing member has leading and trailing ends that define a longitudinal axis. The inner member is operably associated with the housing member and includes one or more longitudinal portals extending therethrough adapted for substantially sealed reception of a surgical object. The inner member may be less compliant than the housing member. The inner member may rotate about the longitudinal axis of the housing member.

12 Claims, 2 Drawing Sheets

(52) U.S. Cl.
CPC ........ *A61B 17/0218* (2013.01); *A61B 17/3431* (2013.01); *A61B 2017/0225* (2013.01); *A61B 2017/3429* (2013.01); *A61B 2017/3445* (2013.01); *A61B 2017/3486* (2013.01)

(56) References Cited

U.S. PATENT DOCUMENTS

| | | | |
|---|---|---|---|
| 4,688,568 | A | 8/1987 | Frass et al. |
| 5,183,471 | A | 2/1993 | Wilk |
| 5,257,973 | A | 11/1993 | Villasuso |
| 5,375,588 | A | 12/1994 | Yoon |
| 5,490,843 | A | 2/1996 | Hildwein et al. |
| 5,653,705 | A | 8/1997 | de la Torre et al. |
| 5,672,168 | A | 9/1997 | de la Torre et al. |
| 5,842,971 | A | 12/1998 | Yoon |
| 6,197,002 | B1 | 3/2001 | Peterson |
| 6,454,783 | B1 | 9/2002 | Piskun |
| 7,052,456 | B2 | 5/2006 | Simon |
| 7,223,257 | B2 | 5/2007 | Shubayev et al. |
| 7,798,898 | B2 | 9/2010 | Luciano, Jr. et al. |
| 8,968,190 | B2 * | 3/2015 | Stopek ............... A61B 17/3423 600/205 |
| 2005/0096695 | A1 | 5/2005 | Olich |
| 2006/0200003 | A1 | 9/2006 | Youssef |
| 2006/0247499 | A1 | 11/2006 | Butler et al. |
| 2006/0247673 | A1 | 11/2006 | Voegele et al. |
| 2007/0060884 | A1* | 3/2007 | Hayek ............... A61B 17/3423 604/104 |
| 2007/0208312 | A1 | 9/2007 | Norton et al. |
| 2008/0097515 | A1 | 4/2008 | Chang et al. |
| 2009/0093752 | A1* | 4/2009 | Richard ............ A61B 17/3423 604/24 |
| 2009/0326332 | A1 | 12/2009 | Carter |
| 2010/0249525 | A1 | 9/2010 | Shelton, IV et al. |
| 2010/0312065 | A1* | 12/2010 | Shelton, IV ........ A61B 17/3423 600/207 |

FOREIGN PATENT DOCUMENTS

| | | |
|---|---|---|
| EP | 2044889 A1 | 4/2009 |
| EP | 2098182 A2 | 9/2009 |
| GB | 2442940 A | 4/2008 |
| WO | 97/33520 | 9/1997 |
| WO | 99/16368 | 4/1999 |
| WO | 01/49363 | 7/2001 |
| WO | 2008/042005 | 4/2008 |
| WO | 2008/093313 | 8/2008 |
| WO | 2008/121294 A1 | 10/2008 |
| WO | 2009046164 A1 | 4/2009 |
| WO | 2009094476 A1 | 7/2009 |

OTHER PUBLICATIONS

European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
U.S. Appl. No. 12/961,560, filed Dec. 7, 2010, David Farascioni.
U.S. Appl. No. 13/091,246, filed Apr. 21, 2011, Paul D. Richard.
U.S. Appl. No. 13/030,164, filed Feb. 18, 2011, Gennady Kleyman.
U.S. Appl. No. 13/030,172, filed Feb. 18, 2011, Gennady Kleyman.
U.S. Appl. No. 13/030,178, filed Feb. 18, 2011, Gennady Kleyman.
U.S. Appl. No. 13/031,346, filed Feb. 21, 2011, Gennady Kleyman.
U.S. Appl. No. 13/031,352, filed Feb. 21, 2011, Gennady Kleyman.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.

* cited by examiner

SINGLE INCISION SURGICAL PORTAL APPARATUS INCLUDING INNER MEMBER

CROSS-REFERENCE TO RELATED APPLICATIONS

This application is a continuation application of U.S. patent application Ser. No. 12/796,330, filed on Jun. 8, 2010, which claims the benefit of U.S. Provisional Patent Application Ser. No. 61/236,652, filed on Aug. 25, 2009, the entire contents of each of which are incorporated by reference herein.

BACKGROUND

1. Technical Field

The present disclosure relates generally to a single incision surgical portal apparatus for use in minimally invasive surgical procedures, such as endoscopic or laparoscopic type procedures, (or open surgical procedures) and more particularly to an apparatus for introducing one or more instruments into a body cavity.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gas are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various ports with valves and seals are used during the course of minimally invasive procedures and are widely known in the art. However, a continuing need exists for a surgical portal apparatus that can facilitate the accessibility of an underlying tissue site with relative ease and with minor inconvenience for the surgeon.

SUMMARY

The present disclosure is directed to a surgical portal apparatus including a housing member and an inner member. The housing member includes an expandable material that is adapted to transition between a compressed condition and an expanded condition. In the expanded condition, an outer surface of the housing member is adapted for a substantial sealing relationship with tissue upon insertion of the housing member within the tissue for accessing an underlying tissue site. The housing member has leading and trailing ends that define a longitudinal axis. The housing member defines a longitudinal passage for accommodating the inner member therein.

The inner member is operably associated with the housing member and includes one or more longitudinal ports extending therethrough adapted for substantially sealed reception of a surgical object. The inner member may be less compliant than the housing member. The inner member may rotate about the longitudinal axis of the housing member. In embodiments, the inner member is removable. In embodiments, one or more ports may have a diameter different from one or more of the other ports. The inner member may be substantially cylindrical. In embodiments, the inner member is comprised of an expandable material.

In embodiments, the inner member and the housing member may be disposed in substantial sealing relationship. One or both of the inner member and the housing member may be comprised of an elastomeric material.

BRIEF DESCRIPTION OF THE DRAWINGS

Various embodiments of the present disclosure are described hereinbelow with reference to the drawings, wherein.

DETAILED DESCRIPTION OF EMBODIMENTS

Figure 1:
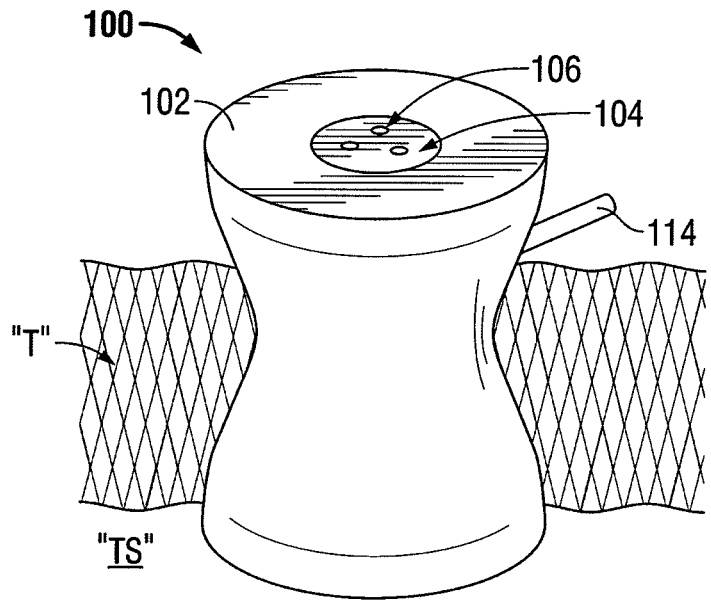
FIG. 1 is a perspective view of a surgical portal apparatus having a housing member and an inner member in accordance with the present disclosure.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

One type of minimal invasive surgery described herein is multiple instrument access through a single surgical port, e.g., SILS®. Multiple instrument access through a single surgical port is a minimally invasive surgical procedure, which permits a surgeon to operate through a single entry point, typically the patient's navel. The disclosed multiple instrument access through a single surgical port procedure may involve insufflating the body cavity and positioning a housing member within, e.g., the navel of the patient. Instruments including an endoscope and additional instruments such as graspers, staplers, forceps or the like may be introduced within the housing member to carry out the surgical procedure.

Referring now to the drawings, in which like reference numerals identify identical or substantially similar parts throughout the several views, FIG. 1 illustrates a surgical portal apparatus 100 that may be used in any endoscopic, laparoscopic and/or open surgical procedure. Surgical portal apparatus 100 includes a housing member 102 and an inner member 104 in accordance with the principles of the present disclosure. Inner member 104 is depicted enclosed within housing member 102 in FIG. 1. As best depicted in FIG. 1, housing member 102 is adapted for insertion within a tissue tract "T", e.g., through the abdominal or peritoneal lining in connection with a laparoscopic surgical procedure. However, housing member 102 is adapted for insertion within any opening in a patient's skin (e.g., an incision or any naturally occurring orifice such as the anus or vagina). The presently disclosed surgical portal apparatus 100 may be used with a surgically created incision, a naturally occurring opening such as the anus or the vagina, or in non-laparoscopic procedures.

Figure 2:
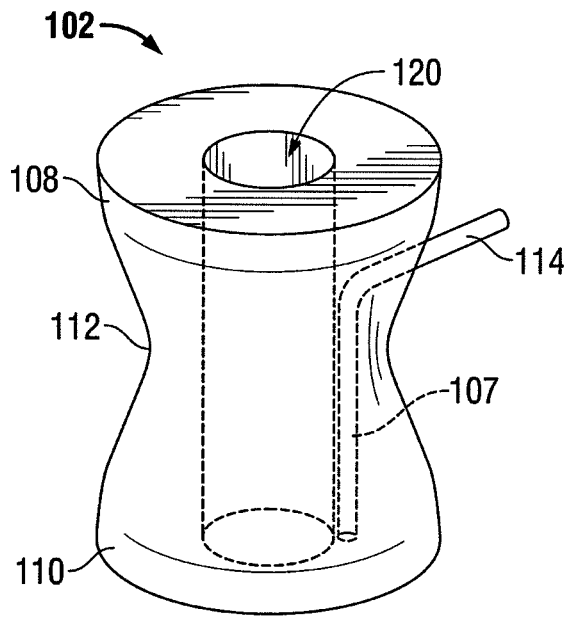
FIG. 2 is a perspective view of the housing member of the surgical portal apparatus of FIG. 1 with the inner member removed.

Referring now to FIGS. 1 and 2, housing member 102 may define an hourglass shape as shown and a longitudinal passage 120 extending therethrough for substantially sealed reception of inner member 104. Either one of both of the housing member 102 and the inner member 104 may include a structure, e.g., a lip, a ring, a groove, etc., for helping to maintain the relative position of the two components. Trailing and leading ends 108, 110 may define flange segments, which may be integrally formed with housing member 102. As best depicted in FIG. 1, when inserted within the tissue tract "T", housing member 102 is adapted to establish a substantial seal within the tract "T", i.e., with the tissue surfaces defining the tract "T." Housing member 102 may be made from a disposable, compressible, and/or flexible type material for example, but not limited to, a suitable foam or gel material having sufficient compliance to form a seal about one or more surgical objects, and also establish a sealing relation with the tissue. The foam is preferably sufficiently compliant to accommodate off axis motion of the surgical object. In one embodiment, the foam includes a polyisoprene material. In embodiments, the material may be elastomeric.

During insertion, housing member 102 may be compressed to a compressed condition to permit at least partial passage through the tract "T." Once within the tract "T", housing member 102 will return toward the normal expanded condition with the outer wall 112 of the housing member 102 establishing a seal with the tissue defining the tissue tract "T." Housing member 102 may include an insufflation conduit 114 disposed in mechanical cooperation with an insufflation port 107 (FIG. 2) and connectable to a source of an insufflation fluid (e.g. $CO_2$) that communicates the insufflation fluid to the work space. The insufflation fluid maintains the work space. An example of such a housing member is disclosed in commonly assigned U.S. patent application Ser. No. 12/244,024, filed Oct. 2, 2008, the entire content of which is hereby incorporated by reference herein.

Figure 3:
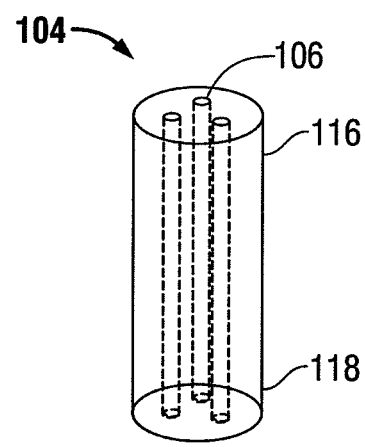
FIG. 3 is a perspective view of the inner member of the surgical portal apparatus of FIG. 1.
Figure 4C:
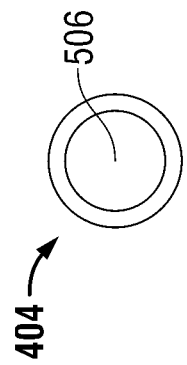
FIG. 4C is top plan view of another embodiment of an inner member in accordance with the present disclosure.
Figure 4B:
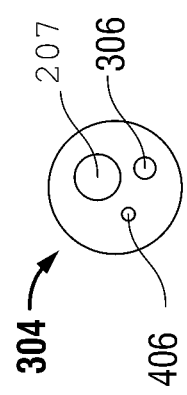
FIG. 4B is top plan view of another embodiment of an inner member in accordance with the present disclosure.
Figure 4A:
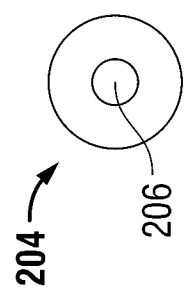
FIG. 4A is top plan view of one embodiment of an inner member in accordance with the present disclosure.

With reference to FIGS. 1 and 3, inner member 104 is adapted to facilitate insertion of instruments within an underlying tissue site "TS." Inner member 104 is substantially elongated and includes a trailing or proximal end 116 and a leading or distal end 118. As depicted in FIG. 3, inner member 102 includes one or more longitudinal ports 106, which may define variously-sized diameters. For example, in embodiments, inner member 102 may include a plurality of longitudinal ports 106a, 106b, 106c, etc. (FIG. 5) extending through the inner member 104. With reference to FIG. 4A-4C, inner member 204 includes one longitudinal port 206, inner member 304 includes longitudinal ports 207, 306, and 406, each defining different diameters, and inner member 404 includes longitudinal port 506, which defines a diameter larger than longitudinal ports 206, 207, 306, and 406. Each of the described ports may be sized from about 5 mm to about 15 mm.

Referring again to FIGS. 1 and 3, one or more of the longitudinal ports 106 are dimensioned to receive a surgical object, e.g. a surgical instrument (not shown) therethrough. Upon introduction through a respective port 106, the inner surface portions defining the port 106 establish and maintain a substantial sealed relation about the instrument or surgical object. Inner member 104 may be made of any type of suitable material, for example, but not limited to, a polymeric material, and may be rigid or flexible (e.g., elastomeric). Inner member 104 may be made from a disposable, compressible, and/or flexible type material for example, but not limited to, a suitable foam or gel material having sufficient compliance to form a seal about one or more surgical objects, and also establish a sealing relation with the longitudinal passage 120 of the housing member 102. The foam is preferably sufficiently compliant to accommodate off axis motion of the surgical object. In one embodiment, the foam includes a polyisoprene material.

In embodiments of the present disclosure, surgical portal apparatus 100 may come preassembled with inner member 104 disposed within housing member 102. In the alternative, inner member 104 may be positioned within housing member 102 at the surgical site.

Figure 5:
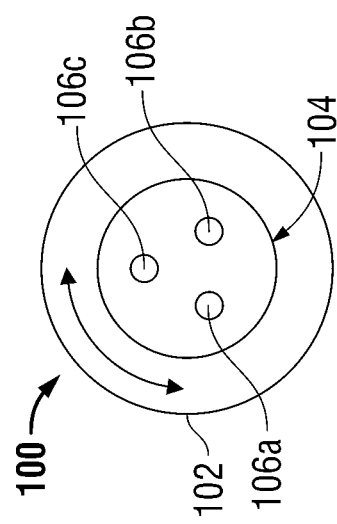
FIG. 5 is a top plan view of the surgical portal apparatus of FIG. 1 shown in a first orientation.

As illustrated in FIG. 5, inner member 104 may rotate relative to housing member 104 for repositioning the longitudinal portals 106a, 106b, 106c in order to facilitate the removal of tissue or to facilitate the accessibility of the underlying tissue site. In addition, the inner member 104 may be completely removed from the housing member 102 for utilizing the longitudinal passage 120 as an access port to the underlying tissue site.

A method of introducing surgical portal apparatus 100 includes positioning leading or distal end 110 of housing member 102 within the tissue tract "T" and advancing the leading end 110 to a predetermined depth (FIG. 1). Once housing member 102 is located within the tissue tract "T", e.g., with trailing and leading ends 108, 110 of the housing member 102 on opposed sides of the body wall (e.g., the abdominal cavity wall); housing member 102 expands toward its normal expanded condition in sealed engagement with the tissue defining the tissue tract. Thereafter, inner member 104 is positioned within proximal or trailing end 108 of housing member 102 (if not preassembled as hereinabove discussed). Upon insertion, inner member 104 compresses to fit within the inner boundary of longitudinal passage 120 of housing member 102. Inner member 104 is advanced relative to tissue tract "T" by either advancing the inner member 104 within housing member 102 or advancing the housing member 102 further into the tract "T." When inner member 104 is located within the longitudinal passage 120 of housing member 102, e.g., with leading and trailing ends 118, 116 of the inner member 104 on opposed sides of the body wall (e.g., the abdominal cavity wall), inner member 104 expands toward its normal expanded condition (which it naturally biases towards regardless of its position relative to the longitudinal passage 120) in sealed engagement with the inner boundary of longitudinal passage 120 of housing member 102. As shown in FIG. 5 and as described above, inner member 104 may then be rotated relative to the housing member 102 or removed therefrom. In addition, inner member 104 may be replaced by another inner member 104 or inner members 204, 304, 404.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

The invention claimed is:

1. A surgical portal apparatus, comprising:
    a housing member having a leading end and a trailing end and defining a longitudinal axis between the leading and trailing ends; and
    an inner member positioned within the housing member and rotatable relative to the housing member about the longitudinal axis of the housing member, at least one port extending longitudinally through the inner member, the inner member having a leading end and a trailing end, the leading end of the housing member and the leading end of the inner member aligned along the longitudinal axis of the housing member such that the leading end of the housing member and the leading end of the inner member are coplanar.

2. The surgical portal apparatus according to claim 1, wherein the housing member is formed of a material configured to transition between a compressed condition and an expanded condition.

3. The surgical portal apparatus according to claim 1, wherein the inner member is formed of a first material and the housing member is formed of a second material, the first material being less compliant than the second material.

4. The surgical portal apparatus according to claim 1, wherein the housing member defines a passage that extends longitudinally through the housing member, the inner member being removably received in the passage of the housing member.

5. The surgical portal apparatus according to claim 1, wherein the at least one port includes a first port and a second port, the first port having a diameter different from a diameter of the second port.

6. The surgical portal apparatus according to claim 1, wherein the inner member is cylindrical.

7. The surgical portal apparatus according to claim 1, wherein at least one of the inner member or the housing member is fabricated from an elastomeric material.

8. The surgical portal apparatus according to claim 1, wherein the housing member has an hour-glass shape.

9. The surgical portal apparatus according to claim 1, wherein the housing member is fabricated from at least one of:
    a foam; or
    a gel.

10. The surgical portal apparatus according to claim 1, wherein the housing member has an outer surface configured to secure to tissue while positioned in an opening formed within tissue.

11. The surgical portal apparatus according to claim 1, wherein the trailing end of the housing member and the trailing end of the inner member are aligned along the longitudinal axis of the housing member such that the trailing end of the housing member and the trailing end of the inner member are coplanar.

12. The surgical portal apparatus according to claim 1, wherein the inner member is solid.

* * * * *